(12) United States Patent
Dou et al.

(10) Patent No.: US 10,111,616 B2
(45) Date of Patent: Oct. 30, 2018

(54) APPARATUS, METHOD AND COMPUTER ACCESSIBLE MEDIUM FOR MONITORING SLEEP QUALITY AND APPARATUS THEREOF

(71) Applicant: Shenyang XIKANG ALPS Technologies Co., Ltd., Liaoning (CN)

(72) Inventors: Yuanzhu Dou, Liaoning (CN); Lu Zhao, Liaoning (CN)

(73) Assignee: NEUSOFT XIKANG ALPS (SHENYANG) TECHNOLOGY CO., LTD., Shenyang, Liaoning Province (CN)

( * ) Notice: Subject to any disclaimer, the term of this patent is extended or adjusted under 35 U.S.C. 154(b) by 484 days.

(21) Appl. No.: 14/576,451

(22) Filed: Dec. 19, 2014

(65) Prior Publication Data
US 2015/0182162 A1 Jul. 2, 2015

(30) Foreign Application Priority Data
Dec. 26, 2013 (CN) .......................... 2013 1 0732827

(51) Int. Cl.
*A61B 5/00* (2006.01)
*A61B 5/11* (2006.01)

(52) U.S. Cl.
CPC .......... *A61B 5/4815* (2013.01); *A61B 5/1118* (2013.01); *A61B 5/4809* (2013.01); *A61B 5/4812* (2013.01)

(58) Field of Classification Search
CPC ..................... A61B 5/11; A61B 5/1118; A61B 5/113–5/1135; A61B 5/4812;
(Continued)

(56) References Cited

U.S. PATENT DOCUMENTS

2005/0065560 A1* 3/2005 Lee ....................... A61B 5/0809
607/6
2006/0111635 A1* 5/2006 Todros ................. A61B 5/0402
600/484
(Continued)

FOREIGN PATENT DOCUMENTS

CN 1852681 A 10/2006
CN 101528127 A 9/2009
(Continued)

OTHER PUBLICATIONS

English translation of WO 2013/125048, accessed from JPO translation tool on Sep. 1, 2016, available from https://dossier1.j-platpat.inpit.go.jp/cgi-bin/tran_web_cgi_ejje?u=http://dossier1.j-platpat.inpit.go.jp/tri/translation/201609022304321243498818761175336978DF016B7C7A486E65511328206374C&tt1=patent&tt2=internet&tt3=computerV16&tt4=chemistryV16&tt.*

*Primary Examiner* — Rene Towa
(74) *Attorney, Agent, or Firm* — Hunton Andrews Kurth LLP

(57) ABSTRACT

Method, apparatus and computer-accessible medium for monitoring sleep quality of a user are described. For example, using such exemplary Method, apparatus and computer-accessible medium, it is possible to collect body movement signals of the user during sleep, and calculate body movement energy of a preset time-slot, based on the body movement signals collected during the preset time-slot. It is also possible to calculate an estimation threshold of a preset estimation time-span including the preset time-slot, based on body movement energy of preset time-slots which are included in the preset estimated time-span. Further, a determination can be made as to a sleep state of the user based on a comparison between the body movement energy of the preset time-slot and the estimation threshold of the preset estimation time-span. Such exemplary Method,
(Continued)

apparatus and computer-accessible medium facilitate a strong adaptive ability and highly reliable sleep monitoring.

11 Claims, 1 Drawing Sheet

(58) Field of Classification Search
CPC ... A61B 5/4815; A61B 5/7221; A61B 5/0538; A61B 5/4255; A61B 1/00082; A61B 5/6853; A61B 5/053
See application file for complete search history.

(56) References Cited

U.S. PATENT DOCUMENTS

| | | | | |
|---|---|---|---|---|
| 2008/0234785 | A1* | 9/2008 | Nakayama | A61B 5/0205 607/62 |
| 2008/0306396 | A1* | 12/2008 | Ariav | A61B 5/113 600/527 |
| 2009/0203972 | A1* | 8/2009 | Heneghan | A61B 5/0507 600/301 |
| 2010/0130873 | A1* | 5/2010 | Yuen | A61B 5/0205 600/484 |
| 2011/0178377 | A1* | 7/2011 | Heneghan | G06F 19/3418 600/301 |
| 2012/0289867 | A1* | 11/2012 | Kasama | A61B 5/11 600/595 |
| 2013/0053653 | A1* | 2/2013 | Cuddihy | A61B 5/0205 600/301 |

FOREIGN PATENT DOCUMENTS

| | | |
|---|---|---|
| CN | 102804190 A | 11/2012 |
| JP | 2009247386 A | 10/2009 |
| JP | 4821395 B2 | 11/2011 |
| JP | 859778 B2 | 1/2012 |
| JP | 2013-198666 | 10/2013 |
| WO | WO 2012/035737 A1 | 3/2012 |
| WO | WO 2013125048 A1 * | 8/2013 ........... A61B 5/1135 |

* cited by examiner

APPARATUS, METHOD AND COMPUTER ACCESSIBLE MEDIUM FOR MONITORING SLEEP QUALITY AND APPARATUS THEREOF

CROSS-REFERENCE(S) TO RELATED APPLICATION(S)

This application claims priority to Chinese Patent Application No. 201310732827.7, filed with the State Intellectual Property Office of People's Republic of China on Dec. 26, 2013, the entire disclosure of which is incorporated herein by reference.

FIELD OF THE DISCLOSURE

The present disclosure relates to the technical field of non-contact sleep body movement monitoring, and in particular to apparatus, method and computer-accessible medium for monitoring sleep quality and an apparatus thereof.

BACKGROUND INFORMATION

Sleep quality can provide certain influence to human health. Monitoring at least some physiological parameters in sleeping may not only evaluate the sleep quality, but also provide a valuable diagnostic basis for certain conditions and/or diseases. Thus, analyzing and achieving the non-contact method for monitoring sleep can be of a significant importance.

The monitoring process of the conventional methods and systems for monitoring sleep can include collecting body movement signals from a person to be monitored. A fixed threshold based estimation can be performed each time one signal is collected, to determine a sleep state which the person to be monitored is currently at. If each time one signal is collected, the estimation can performed one time, the collected signal may be subject to an interference. Therefore, an error may be generated in the estimation, and resulting in the counted data is not reliable. There may be different distances from a sensor to the person to be monitored, it causes the sensitivity deviation of the sensor; in addition, the adaptive ability of the fixed threshold based estimation is poor. Thus, the sleep state of the person to be monitored may not be monitored accurately. Accordingly, the conventional methods for monitoring sleep have poor anti-inference ability, poor adaptive ability and/or results in unreliable monitoring result. Further, the conventional methods for monitoring sleep may not meet the preference of strong adaptive ability and highly reliable sleep monitoring application.

Accordingly, there is a need to address at least some of the issued and/or deficiencies described herein above.

SUMMARY OF EXEMPLARY EMBODIMENTS

In order to address and/or at least partially solve at least some of the problems described above, according to certain exemplary embodiments of the present disclosure, apparatus, method and computer-accessible medium can be provided for monitoring sleep quality to meet and/or address the preferences of strong adaptive ability and highly reliable sleep monitoring application.

To that end, with such exemplary apparatus, method and computer-accessible medium can be used to collect body movement signals of a user during sleep, calculate body movement energy of a preset time-slot, based on the body movement signals collected during the preset time-slot, and calculate an estimation threshold of a preset estimation time-span including the preset time-slot, based on body movement energy of preset time-slots which are included in the preset estimation time-span. Further, it is possible to determine a sleep state of the user based on a comparison between the body movement energy of the preset time-slot and the estimation threshold of the preset estimation time-span.

According to further exemplary embodiments of the present disclosure, the calculation of body movement energy of the preset time-slot can be performed (e.g., using a pre-programmed computer) based on the body movement signals collected during the preset time-slot. Such exemplary calculation can include obtaining in sequence the body movement signals collected during the preset time-slot at the end of the preset time-slot, and calculating a sum of the obtained body movement signals to obtain the body movement energy of the preset time-slot.

In other (possibly additional) exemplary embodiments of the present disclosure, the calculation of the estimation threshold of the preset estimation time-span can include extracting in sequence the body movement energy of the preset time-slots at the end of the preset estimation time-span, and calculating an average value of the extracted body movement energy to obtain the estimation threshold of the preset estimation time-span.

According to yet other (possibly additional) exemplary embodiments of the present disclosure, the determination of the sleep state of the user can include calculating a ratio of the body movement energy of the preset time-slot to the estimation threshold of the preset estimation time-span, and determining the sleep stage of the user in the preset time-slot based on the calculated ratio, where the sleep stage includes a stage of deep sleep, a stage of light sleep, a stage of intermediate sleep and an awake stage.

In still further (possibly additional) exemplary embodiments of the present disclosure, the determination of the sleep stage of the user can include (i) determining that the user is at the stage of deep sleep in the case that the calculated ratio is less than a first threshold, (ii) determining that the user is at the stage of intermediate sleep in the case that the calculated ratio is greater than the first threshold and less than a second threshold, (iii) determining that the user is at the stage of light sleep in the case that the calculated ratio is greater than the second threshold and less than a third threshold, and (iv) determining that the user is at the awake stage in the case that the calculated ratio is greater than the third threshold. For example, the third threshold can be greater than the second threshold, and the second threshold can be greater than the first threshold.

The apparatus for monitoring sleep quality according to an exemplary embodiment of the present disclosure can include/comprise a collecting unit/system/module configured to cause a computer to collect body movement signals of a user during sleep. The apparatus can also include an energy calculating unit/system/module configured to cause the computer to calculate body movement energy of a preset time-slot based on the body movement signals collected during the preset time-slot. The apparatus can further comprise a threshold calculating unit/system/module configured to cause the computer to calculate a estimation threshold of a preset estimation time-span including the preset time-slot, based on body movement energy of preset time-slots which are included in the preset estimation time-span. In addition, the exemplary apparatus can include a determination unit/ system/module configured to cause the computer to determine a sleep state of the user based on a comparison between the body movement energy of the preset time-slot and the estimation threshold of the preset estimation time-span.

In one exemplary embodiment of the present disclosure, the energy calculating unit/system/module can include an obtaining module configured to cause the computer to obtain in sequence the body movement signals collected during the preset time-slot at the end of the preset time-slot; and an integrating module configured to cause the computer to calculate a sum of the obtained body movement signals to obtain the body movement energy of the preset time-slot.

In addition, according to a further exemplary embodiment of the present disclosure, the threshold calculating cause the computer can includes an extracting module configured to cause the computer to extract in sequence the body movement energy of the preset time-slots at the end of the preset estimation time-span, and an averaging module configured to cause the computer to calculate an average value of the extracted body movement energy to obtain the estimation threshold of the preset estimation time-span.

In an additional exemplary embodiment, the estimation cause the computer can include a ratio module configured to cause the computer to calculate a ratio of the body movement energy of the preset time-slot to the estimation threshold of the preset estimation time-span, and a determination module configured to cause the computer to determine the sleep stage of the user in the preset time-slot based on the calculated ratio, where the sleep stage at least includes a stage of deep sleep, a stage of light sleep, a stage of intermediate sleep and an awake stage.

Further, according to certain exemplary embodiments of the present disclosure, the determination module can include (i) a first determination sub-module configured to cause the computer to determine that the user is at the stage of deep sleep in the case that the calculated ratio is less than a first threshold. (ii) a second determination sub-module configured to cause the computer to determine that the user is at the stage of intermediate sleep in the case that the calculated ratio is greater than the first threshold and less than a second threshold, where the second threshold is greater than the first threshold, (iii) a third determination sub-module configured to cause the computer to determine that the user is at the stage of light sleep in the case that the calculated ratio is greater than the second threshold and less than a third threshold, where the third threshold is greater than the second threshold, and (iv) a fourth determination sub-module, configured to determine that the user is at the awake stage in the case that the calculated ratio is greater than the third threshold.

According to additional exemplary embodiments of the present disclosure, apparatus, method and computer-accessible medium can be provided for monitoring sleep quality and an apparatus thereof to meet and/or address the preference of strong adaptive ability and high reliable sleep monitoring application. As an initial matter, with a pre-programmed computer, e.g., body movement signals of the user in sleep can be collected, and body movement energy of a preset time-slot can be calculated based on the body movement signals collected during the preset time-slot. Due to influence from the movement of local body or the interference from outside radio wave, the measured single body movement signal generally cannot reflect a true state of the user. An error in estimation may occur if the estimation is based on a single body movement signal. Thus, the sleep state can be estimated by a pre-programmed computer based on the body movement energy of a preset time-slot, thereby avoiding the error in estimation based on a single body movement signal. Then, a estimation threshold of a preset estimation time-span (including the preset time-slot) can be calculated by the pre-programmed computer based on body movement energy of preset time-slots, which can be included in the preset estimation time-span; and the sleep state of the user is determined based on a comparison between the body movement energy of the preset time-slot and the estimation threshold of the preset estimation time-span.

In different sleep postures, the distances between the user and a sensor can be different, and thus such configuration may cause monitoring sensitivity deviation, and resulting in an unreliable monitoring result. Thus, the estimation threshold can be adjusted periodically based on the actual sleep condition of the user and the preset estimation time-span, such that the estimation threshold of the preset estimation time-span is fit for determining the sleep state of the user in this estimation time-span, thereby facilitating more reliable estimation results.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

In order to illustrate the technical solutions of the embodiments of the invention or the conventional art more clearly, hereinafter the accompanying drawings for the description of the embodiments or the conventional art will be introduced simply. Obviously, the following described accompanying drawings are only a few of the embodiments, other accompanying drawings may also be obtained by those skilled in the art according to these accompanying drawings without any creative work.

Figure 1:
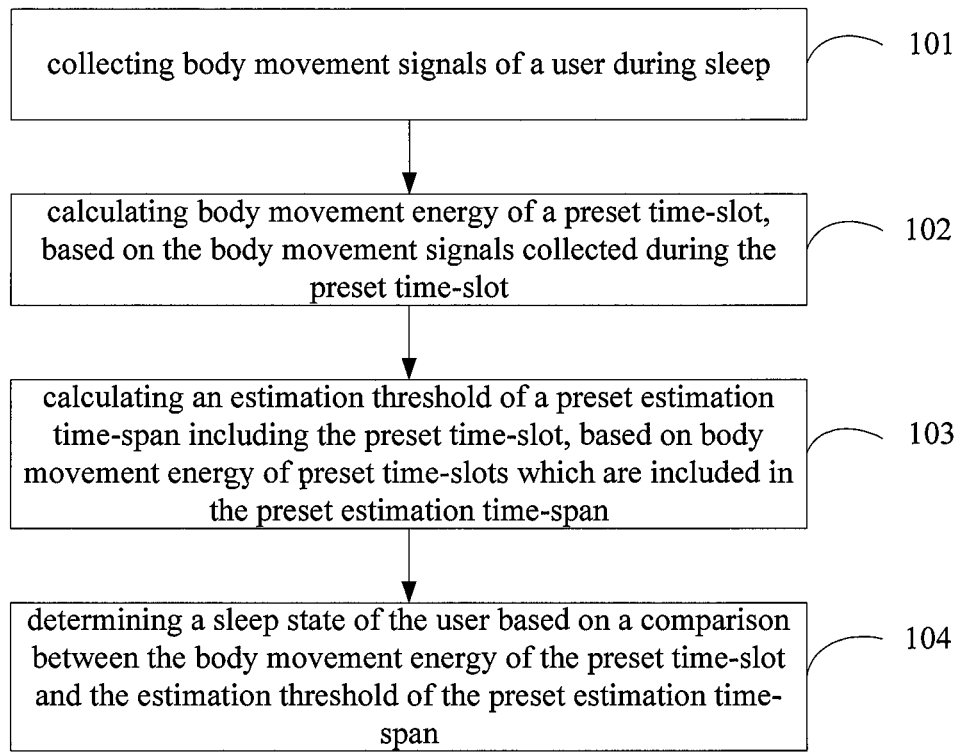
FIG. 1 is a flow chart of a method for monitoring sleep quality according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

FIG. 1 shows a flow chart of a method for monitoring sleep quality according to an exemplary embodiment of the present disclosure, which can include steps/procedures 101 to 104, and can be performed using a pre-programmed computer. Step 101 may include collecting body movement signals of a user during sleep.

For example, multiple types of sensors can be utilized to collect a body movement signal of a user during sleep. In one exemplary embodiment, a radio frequency sensor can be utilized to collect the body movement signal of the user during sleep. The work exemplary use/operation of the radio frequency sensor can be as follows. After an electromagnetic wave transmitted from the radio frequency sensor irradiates a body, the reflected wave can provide and/or carry certain information about the body; movement amount of the body effects the amplitude and the phase of the reflected wave, etc., and the vital movement (such as heartbeat, breathe) of the body causes the micro-movement of the surface of the body. The local signal of sensor transmitter and the reflected signal can be mixed at the sensor to obtain the body movement signal reflecting the sleep state of the body.

In step 102, body movement energy of a preset time-slot can be calculated based on the body movement signals collected during the preset time-slot. For example, when a person is asleep, normal vital movements such as breathe, and heartbeat causes micro-movement of the surface of the body. Body movement signals caused by such movement can be continuously monitored by the radio frequency sensor due to its highly sensitivity. In addition, the body movement signal monitored by the sensor can be propagated as an electromagnetic wave in the air, although it can be susceptible to suffer the interference from other radio wave, and an error in estimation the sleep state may occur. In order to avoid a possible occurrence of the error in estimation the sleep state, in this step/procedure, the sleep state can be determined based on the body movement energy over a preset time-slot, thereby likely reducing or avoiding the error in estimation by estimation only based on the single body movement signal at a certain time.

Such exemplary step 102 can include the performance of certain procedures, as follows. For example, the body movement signals collected during the preset time-slot can be obtained in sequence at the end of the preset time-slot. Further, a sum of the obtained body movement signals can be calculated to obtain the body movement energy of the preset time-slot. The exemplary summing operation described herein may be or include any of an integral operation, an addition operation or a convolution operation. In practice, other summing operations can be utilized, as long as the body movement during the time-slot can be calculated.

In step 103, an estimation threshold of a preset estimation time-span including the preset time-slot can be calculated, e.g., based on body movement energy of preset time-slots which can be included in the preset estimation time-span. For example, the sensitivities of different radio frequency sensors can be different, in different sleep postures, the distances between a person to be monitored and the radio frequency sensor are different, and this can result in monitoring sensitivities deviation of the radio frequency sensor. For the person to be monitored, his or her sleep state can be determined based on the monitored true body movement signal when he sleeps. If a fixed estimation threshold is adopted without considering the difference of sensitivity of the radio frequency sensors, the estimation result may be at least partially unreliable, and may not accurately reflect the sleep state of the person. In this exemplary case, the estimation of the threshold can be adjusted, e.g., periodically, based on the body movement signals monitored by the radio frequency sensor, such that the estimation threshold can correct the sensitivity difference caused by the sleep posture of the person monitored and the distance as well as the sensitivity difference caused by the radio frequency sensor itself, thereby improving the accuracy of the estimation.

Such exemplary step/procedure 103 can include an extraction of the body movement energy of the preset time-slots which are included in the preset estimation time-span, e.g., in sequence, at the end of the preset estimation time-span. Further, an average value of the extracted body movement energy can be calculated to obtain an estimation threshold of the preset estimation time-span.

In step 104, a sleep state of the user can be determined based on a comparison between the body movement energy of the preset time-slot and the estimation threshold of the preset estimation time-span. This exemplary step/procedure 104 can include a calculation of a ratio of the body movement energy of the preset time-slot to the estimation threshold of the preset estimation time-span, and a determination of the sleep stage of the user in the preset time-slot based on the calculated ratio, where the sleep stage at least can include a stage of deep sleep, a stage of light sleep, a stage of intermediate sleep and an awake stage.

Optionally, alternatively or in addition, the determination of the sleep stage of the user in the preset time-slot may include one or more of the following:
  a determination that the user is at the stage of deep sleep in the case that the calculated ratio is less than a first threshold;
  a determination that the user is at the stage of intermediate sleep in the case that the calculated ratio is greater than the first threshold and less than a second threshold
  a determination that the user is at the state of light sleep in the case that the calculated ratio is greater than the second threshold and less than a third threshold; and/or
  a determination that the user is at the stage of the awake stage in the case that the calculated ratio is greater than the third threshold; where the third threshold is greater than second threshold and the second threshold is greater than the first threshold.

In such exemplary case, the sleep state of the user in each preset time-slot may be accurately determined based on the body movement signal collected during the user sleeps, and the sleep quality of the user may be determined based on the duration of each sleep state.

According to certain exemplary embodiments of the present disclosure, a method for monitoring sleep quality can be provided to meet the requirement of strong adaptive ability and highly reliable sleep monitoring application, e.g., using a pre-programmed computer which has been programmed using software to perform certain exemplary procedures described herein. As an initial matter, body movement signals of the user during sleep can be collected in sequence, and body movement energy of a time-slot can be calculated based on a body movement signals collected during the preset time-slot. Due to influence from the movement of local body or the interference from outside radio wave, the measured single body movement signal generally may not reflect a true sleep state of the user. An error in estimation may occur if the estimation is based on a single body movement signal. Hence, the sleep state is determined based on the body movement energy of a preset time-slot, thereby avoiding the error in estimation by estimation based on a single body movement signal. Then, a estimation threshold of a preset estimation time-span including the preset time-slot can be calculated based on body movement energy of preset time-slots which are included in the preset estimation time-span; and the sleep state of the user is determined based on a comparison between the body movement energy of the preset time-slot and the estimation threshold of the preset estimation time-span. In different sleep postures, the distances between the user and a sensor can be different, which may cause a monitoring sensitivity deviation, likely resulting in an unreliable monitoring result. Thus, the estimation threshold can be adjusted periodically based on the actual sleep condition of the user and the preset estimation time-span, such that the estimation threshold of the preset estimation time-span is fit for determining the sleep state of the user in this estimation time-span, thereby facilitating the estimation result to be more reliable.

In addition, according to certain exemplary embodiment of the method for monitoring sleep quality according to the present disclosure, the sleep state can be determined periodically, and the duration of each sleep stage can be also counted, to obtain a report about the sleep quality. In this exemplary manner, reliable basis for adjusting the sleep can be provided to obtain the optimum sleep quality.

In calculating the estimation threshold of each estimation time-span according to the exemplary steps/procedures described above, the interference from the micro-movement of the body and the occasional outside radio wave can be considered to likely improve the accuracy of the estimation threshold. In this case, according to further exemplary embodiments of the present disclosure, based on the first embodiment described above, in step 103, before calculating the estimation threshold of the preset estimation time-span, the body movement energy out of a preset range can be reduce or eliminated, and then the estimation threshold for the preset estimation time-span can be calculated based on the remaining body movement energy.

Therefore, according to one exemplary embodiment, the process for calculating the estimation threshold of the preset estimation time-span can include:

- an extraction of the body movement energy of the preset time-slots which are included in the preset estimation time-span in sequence at the end of the preset estimation time-span;
- an elimination or a reduction of the body movement energy out of a preset range is eliminated from the extracted body movement energy; and/or
- a calculation of an average value of the remaining body movement energy to obtain a estimation threshold of the preset estimation time-span.

For example, the interference from the micro-movement of the body and the occasional outside radio wave may be reduce and/or removed, thereby likely improving the calculating accuracy for the estimation threshold.

In one exemplary embodiment of the present disclosure, for example, a sampling rate can be about 100 Hz, a preset time-slot can be about 90 s and a preset estimation time-span can be about 3600 s.

In this exemplary embodiment, a first step, e.g., step S1, may include a collection of body movement signals of a user during sleep in sequence. For example, a variable A can be configured to count the number of the samples, each time one body movement signal is collected, the variable A increases one. At the end of a preset time-slot, the variable A returns to zero. In the embodiment, one body movement signal can be collected every 0.01 s, the preset time-slot can be, e.g., about 90 s. Hence, when the value of A reaches the maximum number of the collecting −9000 during the time-slot, the variable A returns to zero; when a next preset time-slot begins, the variable A counts from one again. Hence, the time for calculating the body movement energy during the time-slot may be identified by the value of the variable A, e.g., the body movement energy is calculated when the value of A reaches 9000.

In addition, e.g., a variable B can be configured to identify the number of the preset time-slots, the time for calculating the estimation threshold of the estimation time-span may be identified by the value of B. Hence, the value of B increases 1 once A returns to zero. When reaching the maximum number of the preset time-slot during each estimation time-span, the variable B returns to zero; when a next estimation time-span begins, the variable B counts from one again. In the embodiment, since the estimation time-span is 3600 s being equivalent to 40 preset time-slots, therefore an estimation threshold is calculated once B reaches 40, and the value of B returns to zero.

The next exemplary step, i.e., step S2, may include calculating the body movement energy collected during each time-slot is calculated in sequence based on the body movement signals collected during the each preset time-slot of about 90 s. For example, when the variable A reaches 9000, that is to say, when 9000 body movement signals are collected, the body movement energy is calculated one time by integrating computation at the end of the preset time-slot. For example, the body movement energy of the 9000 body movement signals collected during the 90 s is calculated by the trapezoidal integrating computation. In this case, in accordance with the collecting order and collecting time, the body movement energy is calculated when each time 9000 body movement signals are collected, that is to say, each time the variable A reaches 9000, the body movement energy is calculated one time, and the calculated body movement energy during each time-slot is cached, being ready for both the subsequent estimation threshold calculation and the subsequent sleep state determination.

Indeed, e.g., the sample rate can be set as other values in advance, the time-slot may be set as other values, thereby it can be determined that the body movement energy is calculated one time when how many body movement signals are collected based on the time-slot and the sample rate, it is illustrated by taking the parameters described above as an example herein.

The following exemplary step, i.e., step S3, can include calculating an estimation threshold of the preset estimation time-span based on the body movement energy calculated during the preset estimation time-span. Each time the variable B reaches 40, it can be indicated that the preset estimation time-span about 3600 s expires, at which an estimation threshold is calculated, the estimation threshold is used to determine the sleep state of the user to be monitored during the 40 preset time-slots.

For example, the body movement energy of each time-slot can be calculated based on the preset time-slot. The body movement energy calculated of time-slot 1 is N1, the body movement energy calculated of time-slot 2 is N2, the body movement energy calculated of time-slot 3 is N3, and so on, the body movement calculated of time-slot 40 is N40. When the value of the variable B reaches 40, i.e., the variable A performs returning to zero for 40 times, 40 time-slots is passed, at this time a estimation threshold corresponding to the estimation time-span is calculated based on the 40 body movement energy values calculated during the estimation time-span, the estimation threshold is used to determine the sleep state of the user to be monitored during time-slot 1 to time-slot 40. In this case, one estimation threshold is calculated every 40 time-slots.

Indeed, the exemplary estimation time-span can be set as other values, the preset time-slot can be set as other values, it can be determined that the estimation threshold is calculated one time when how many body energy values are calculated based on the time-slot and the estimation time-span, it is illustrated only by taking the parameters described above as an example herein.

A further exemplary step, i.e., step S4, may include determining a sleep state of the user based on a comparison between the body movement energy collected during each preset time-slot and the estimation threshold of the corresponding preset estimation time-span in sequence. The sleep state of the user can be determined based on a comparison between the body movement energy collected during each time-slot and the estimation threshold of the corresponding preset estimation time-span in sequence.

A ratio of the obtained body movement energy of a time-slot to the corresponding estimation threshold can be calculated, and the sleep stage of the user during the time-slot is determined based on the ratio. It can be determined that the user is at the stage of the deep sleep in the case that the ratio is less than, e.g., about 1.2. Further, it can be determined that the user is at the stage of intermediate sleep in the case that the ratio is greater than about 1.2 and less than about 1.4. In addition, it can be determined that the user is at the stage of light sleep in the case that the ratio is greater than about 1.4 and less than about 1.6. Further, it is determined that the user is at the awake stage in the case that the ratio is greater than about 1.6.

According to the exemplary embodiment of the method, system and computer-accessible medium for monitoring the sleep quality according to the present disclosure, e.g., using a pre-programmed computer, the sleep state of the person to be monitored can be determined periodically by taking the body movement energy as baseline data, and the estimation can be is calculated by utilizing the actual body movement signals of the person to be monitored. Thus, the requirement or preference of strong adaptive ability and high reliable monitoring result proposed by the user can be met for sleep monitoring.

Figure 2:
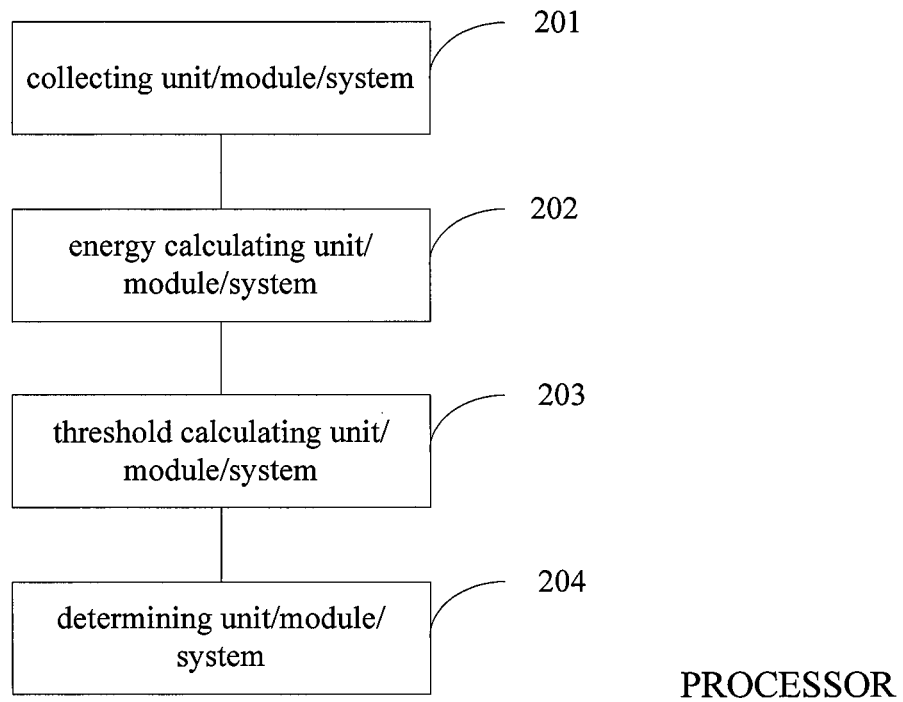
FIG. 2 is a block diagram of an apparatus for monitoring sleep quality according to an exemplary embodiment of the present disclosure.

Corresponding to the exemplary embodiment described herein, according to a further exemplary embodiment of the present disclosure, an apparatus for monitoring sleep quality can be provided. For example, FIG. 2 shows a block diagram of the apparatus for monitoring sleep quality according to an exemplary embodiment of the present disclosure. The exemplary apparatus includes a collecting unit/system/module 201, an energy calculating unit/system/module 202, a threshold calculating unit/system/module 203 and a determination unit/system/module 204. Such exemplary units/systems/modules can be provided in or on a computer arrangement or separately therefrom.

The collecting unit/system/module 201 can be configured to collect body movement signals of a user during sleep (e.g., using the processor of the computer arrangement). The energy calculating unit/system/module 201 can be configured to calculate body movement energy of a preset time-slot based on the body movement signals collected during the preset time-slot (e.g., using the processor of the computer arrangement). The threshold calculating unit/system/module 203 is configured to calculate an estimation threshold of a preset estimation time-span including the preset time-slot, based on body movement energy of preset time-slots which are included in the preset estimation time-span (e.g., using the processor of the computer arrangement).

The determination unit/system/module 204 can be configured to determine a sleep state of the user based on a comparison between the body movement energy of the preset time-slot and the estimation threshold of the preset estimation time-span (e.g., using the processor of the computer arrangement).

Optionally, the energy calculating unit/system/module can includes an obtaining module which can configure the processor to obtain in sequence the body movement signals collected during the preset time-slot at the end of the preset time-slot; and an integrating module which can configure the processor to calculate a sum of the obtained body movement signals to obtain the body movement energy of the preset time-slot.

Optionally (in addition or alternatively), the summing operation adopted by the integrating module may be any of an integral operation, an addition operation and/or a convolution operation. As a matter of course, in practice other summing operations may also be adopted.

Further optionally (in addition or alternatively), the threshold calculating unit/system/module can include an extracting module which can configure the processor to extract in sequence the body movement energy of the preset time-slots at the end of the preset estimation time-span; and an averaging module which can configure the processor to calculate an average value of the extracted body movement energy to obtain the estimation threshold of the preset estimation time-span.

Still further optionally (in addition or alternatively), the estimation unit/system/module can includes a ratio module which can configure the processor to calculate a ratio of the body movement energy of the preset time-slot to the estimation threshold of the preset estimation time-span, and a determination module which can configure the processor to determine the sleep stage of the user in the preset time-slot based on the calculated ratio. The sleep stage can include a stage of deep sleep, a stage of light sleep, a stage of intermediate sleep and/or an awake stage.

Yet further optionally (in addition or alternatively), the estimation module can includes
 a first determination sub-module which can configure the processor to determine that the user is at the stage of deep sleep in the case that the calculated ratio is less than a first threshold;
 a second determination sub-module which can configure the processor to determine that the user is at the stage of intermediate sleep in the case that the calculated ratio is greater than the first threshold and less than a second threshold, where the second threshold is greater than the first threshold;
 a third determination sub-module which can configure the processor to determine that the user is at the stage of light sleep in the case that the calculated ratio is greater than the second threshold and less than a third threshold, where the third threshold is greater than the second threshold; and
 a fourth determination sub-module which can configure the processor to determine that the user is at the awake stage in the case that the calculated ratio is greater than the third threshold.

In addition, in order to improve the accuracy for the estimation threshold calculated by the threshold calculating unit/system/module, the threshold calculating unit/system/module may include:
 a second extracting module which can configure the processor to extract in sequence the body movement of preset time-slots which included in the preset estimation time-span at the end of the preset estimation time-span;
 an eliminating module which can configure the processor to eliminate the body movement energy out of a preset amplitude from the extracted body movement energy; and
 a second averaging module which can configure the processor to calculate an average value of the remaining body movement energy to obtain the estimation threshold of the preset estimation time-span.

Optionally, e.g., the first threshold may be set as about 1.2, the second threshold may be set as about 1.4, and the third threshold may be set as about 1.6.

According to the apparatus for monitoring sleep quality according to an exemplary embodiment of the present disclosure, in order to meet the requirement or the preference of strong adaptive ability and highly reliable monitoring result suggested by the user for sleep monitoring, the body movement energy of a preset time-slot can function as baseline data for the subsequent determining of sleep states. Thus, the error in estimation only based on single body movement signal can be reduce or avoided. The estimation threshold can be adjusted periodically based on the actual sleep condition of the user and the preset estimation time-span, such that the estimation threshold for each time-span is fit for determining the sleep state of the user in this estimation time-span, thereby facilitating the estimation result as being more reliable.

For example, each exemplary embodiment of the present disclosure is described in a progressive way, with the emphasis of each of the exemplary embodiments on the difference between it and the other embodiments; hence, for the same or similar part between the embodiments, one can refer to the other embodiments. For the system or the apparatus disclosed by the exemplary embodiments, since such exemplary embodiment can correspond to the method disclosed by the exemplary embodiments, the description is simplified, for the related part, one can refer to the illustration of the method part.

It also should be noted that, in the context, the relation term such as a first and a second is only used to distinguish one entity or operation from another entity or operation, instead of requiring or indicating that these entities or operations have such relation or order. Furthermore, terms "comprising", "including" and any other variations thereof are intended to be inclusive, such that the process, the method, the article or the device including a series of elements not only include these elements, but also include other elements which are not definitely listed, or also include inherent elements of the process, the method, the article and the device. Without more limitation, elements defined by a sentence "including an/a . . . " do not exclude there are further same elements in the process, method, apparatus, computer-accessible medium, article or the device for the elements.

The exemplary steps of the method or the algorithm described in combination with the exemplary embodiments herein may be implemented by hardware, a software module executed by the processor or a combination thereof. The software module may be disposed in a Random Access Memory (RAM), a memory, a Read Only Memory (ROM), an electrically programmable ROM, an electrically erasable and programmable ROM, a register, a hard disc, a mobile hardware, a CD-ROM or any other forms of storage mediums being well known in the technical field.

The above description of the disclosed embodiments herein enables those skilled in the art to implement or use the disclosure. Various modifications to these embodiments will be apparent to those skilled in the art, the general principle defined herein can be implemented in other embodiments without deviation from the spirit or scope of the disclosure. Therefore, the disclosure is not limited to the illustrated embodiments, but in accordance with the widest scope consistent with the principles and novel features disclosed herein.

What is claimed is:

1. A method for monitoring sleep quality of a user, comprising:

with a radio frequency (RF) sensor located in a specifically-programmed computer, collecting RF body movement signals of a user during sleep;

with the specifically-programmed computer, calculating body movement energy of a preset time-slot, based on the RF body movement signals collected during the preset time-slot, wherein the preset time-slot is one of a plurality of preset time-slots comprised in a preset estimation time-span;

with the programmed computer, calculating an estimation threshold of the preset estimation time-span, based on an average value of the body movement energy of the plurality of preset time-slots which are comprised in the preset estimation time-span;

with the programmed computer, determining a sleep state of the user in the preset time-slot based on a comparison between the body movement energy of the preset time-slot and the estimation threshold of the preset estimation time-span, wherein the determining of the sleep state includes determining the sleep state that is at least one of a stage of deep sleep, a stage of light sleep, a stage of intermediate sleep or an awake stage; and monitoring the sleep quality of the user based on the determined sleep state of the user.

2. The method according to claim 1, wherein the calculating of the body movement energy comprises:

obtaining, in sequence, the RF body movement signals collected during the preset time-slot at an end of the preset time-slot; and calculating a sum of the obtained RF body movement signals to determine the body movement energy of the preset time-slot.

3. The method according to claim 1, wherein the calculating of the estimation threshold comprises:

extracting, in sequence, the body movement energy of the plurality of preset time-slots at an end of the preset estimation time-span; and calculating the average value of the extracted body movement energy to calculate the estimation threshold.

4. The method according to claim 1, wherein the determining of the sleep state comprises:

calculating a ratio of the body movement energy of the preset time-slot to the estimation threshold; and determining the sleep stage of the user in the preset time-slot based on the calculated ratio.

5. The method according to claim 4, wherein the determining of the sleep stage comprises:

determining that the user is at the stage of deep sleep when the calculated ratio is less than a first pre-assigned threshold;

determining that the user is at the stage of intermediate sleep when the calculated ratio is greater than the first threshold and less than a second pre-assigned threshold;

determining that the user is at the stage of light sleep when the calculated ratio is greater than the second threshold and less than a third pre-assigned threshold; and determining that the user is at the awake stage when the calculated ratio is greater than the third pre-assigned threshold, wherein the third threshold is greater than the second threshold, and wherein the second threshold is greater than the first threshold.

6. An apparatus for monitoring sleep quality of a user, comprising:
a computer processor;
a memory storing program instructions,
wherein the computer processor executes the program instructions to:
calculate body movement energy of a preset time-slot, based on radio frequency (RF) body movement signals collected by a RF sensor during the preset time-slot, wherein the preset time-slot is one of a plurality of preset time-slots comprised in a preset time-span;
calculate an estimation threshold of the preset estimation time-span, based on an average value of the body movement energy of the plurality of preset time-slots which are comprised in the preset estimation time-span;
determine a sleep state of the user in the preset time-slot based on a comparison between the body movement energy of the preset time-slot and the estimation threshold of the preset estimation time-span, wherein the determining of the sleep state includes determining the sleep state that is at least one of a stage of deep sleep, a stage of light sleep, a stage of intermediate sleep or an awake stage; and
monitor the sleep quality of the user based on the determined sleep state of the user.

7. The apparatus according to claim 6, wherein the computer processor executes the program instructions to:
obtain, in sequence, the RF body movement signals collected during the preset time-slot at an end of the preset time-slot, and
calculate a sum of the RF obtained body movement signals to determine the body movement energy of the preset time-slot.

8. The apparatus according to claim 6, wherein the computer processor executes the program instructions to:
extract, in sequence, the body movement energy of the plurality of preset time-slots at an end of the preset estimation time-span, and
calculate the average value of the extracted body movement energy to obtain the estimation threshold of the preset estimation time-span.

9. The apparatus according to claim 6, wherein the computer processor executes the program instructions to:
calculate a ratio of the body movement energy of the preset time-slot to the estimation threshold; and
determine the sleep stage of the user in the preset time-slot based on the calculated ratio.

10. The apparatus according to claim 9, wherein the computer processor executes the program instructions to:
determine that the user is at the stage of deep sleep when the calculated ratio is less than a first pre-assigned threshold,
determine that the user is at the stage of intermediate sleep when the calculated ratio is greater than the first threshold and less than a second pre-assigned threshold,
determine that the user is at the stage of light sleep when the calculated ratio is greater than the second threshold and less than a third pre-assigned threshold, and
determine that the user is at the awake stage when the calculated ratio is greater than the third pre-assigned threshold, wherein the third threshold is greater than the second threshold, and wherein the second threshold is greater than the first threshold.

11. A non-transitory computer-accessible medium which, when executed by a computer arrangement, configures the computer arrangement to perform procedures comprising:
calculating body movement energy of a preset time-slot, based on radio frequency (RF) body movement signals collected by a RF sensor during the preset time-slot, wherein the preset time-slot is one of a plurality of preset time-slots comprised in a preset estimation time-span;
calculating an estimation threshold of the preset estimation time-span, based on an average value of the body movement energy of the plurality of preset time-slots which are comprised in the preset estimation time-span;
determining a sleep state of the user in the preset time-slot based on a comparison between the body movement energy of the preset time-slot and the estimation threshold of the preset estimation time-span, wherein the determining of the sleep state includes determining the sleep state that is at least one of a stage of deep sleep, a stage of light sleep, a stage of intermediate sleep or an awake stage; and
monitoring a sleep quality of the user during sleep based on the determined sleep state of the user.

* * * * *